US007214390B2

(12) United States Patent
Barone, Jr. et al.

(10) Patent No.: US 7,214,390 B2
(45) Date of Patent: May 8, 2007

(54) TOPICAL COMPOSITIONS FOR ENHANCING SEXUAL RESPONSIVENESS

(75) Inventors: Frank V. Barone, Jr., Staten Island, NY (US); Christopher Jacobsen, Staten Island, NY (US); Kirill Chumenko, Staten Island, NY (US)

(73) Assignee: Barmensen Labs, LLC, Edison, NJ (US)

( * ) Notice: Subject to any disclaimer, the term of this patent is extended or adjusted under 35 U.S.C. 154(b) by 27 days.

(21) Appl. No.: 10/775,574

(22) Filed: Feb. 9, 2004

(65) Prior Publication Data

US 2004/0265400 A1 Dec. 30, 2004

Related U.S. Application Data

(60) Provisional application No. 60/445,624, filed on Feb. 7, 2003.

(51) Int. Cl.
*A61K 36/00* (2006.01)
*A61K 36/889* (2006.01)
(52) U.S. Cl. ........................ 424/725; 424/727
(58) Field of Classification Search ............... 424/725, 424/727
See application file for complete search history.

(56) References Cited

U.S. PATENT DOCUMENTS

| | | | | |
|---|---|---|---|---|
| 5,208,031 A * | 5/1993 | Kelly | ......................... | 424/412 |
| 5,217,997 A | 6/1993 | Levere et al. | | |
| 5,232,935 A | 8/1993 | Colaset et al. | .............. | 514/356 |
| 5,240,945 A | 8/1993 | Warshaw | .................... | 514/356 |
| 5,318,960 A | 6/1994 | Toppos | ....................... | 514/159 |
| 5,428,070 A | 6/1995 | Cooke | | |
| 5,451,407 A | 9/1995 | Cormier et al. | .............. | 424/448 |
| 5,496,827 A | 3/1996 | Patrick | ........................ | 514/310 |
| 5,543,430 A | 8/1996 | Kaesemeyer | | |
| 5,595,753 A | 1/1997 | Hechtman | | |
| 5,767,160 A | 6/1998 | Kaesemeyer | | |
| 5,891,459 A | 4/1999 | Cooke et al. | | |
| 5,895,658 A | 4/1999 | Fossel | | |
| 5,922,332 A | 7/1999 | Fossel | | |
| 5,985,860 A | 11/1999 | Toppo | ........................ | 514/159 |
| 6,007,824 A | 12/1999 | Duckett et al. | | |
| 6,117,872 A | 9/2000 | Maxwell et al. | | |
| 6,207,713 B1 | 3/2001 | Fossel | | |
| 6,294,517 B1 | 9/2001 | Garvey et al. | | |
| 6,323,211 B1 | 11/2001 | Garvey et al. | | |
| 6,340,480 B1 * | 1/2002 | Duckett et al. | .............. | 424/728 |
| 6,368,640 B1 | 4/2002 | Wuh et al. | | |
| 6,428,791 B1 | 8/2002 | Lezdey et al. | | |
| 6,476,037 B1 | 11/2002 | Wallace | | |
| 6,544,563 B2 | 4/2003 | Wuh et al. | | |
| 6,548,087 B1 | 4/2003 | Kent et al. | | |
| 6,548,841 B2 | 4/2003 | Frazier et al. | | |
| 6,579,543 B1 | 6/2003 | McClung | | |
| 6,646,006 B2 | 11/2003 | Cooke et al. | | |
| 6,803,060 B2 * | 10/2004 | Reyes | ........................ | 424/769 |
| 2002/0151592 A2 | 10/2002 | Cooke et al. | | |
| 2002/0165429 A1 | 11/2002 | Thompson | .................... | 600/38 |
| 2002/0183297 A1 | 12/2002 | Niazi | .......................... | 514/178 |
| 2002/0187165 A1 * | 12/2002 | Harbeck | ...................... | 424/400 |
| 2003/0059484 A1 | 3/2003 | Bonte et al. | ................. | 424/9.2 |
| 2003/0077296 A1 * | 4/2003 | Denton et al. | .............. | 424/400 |
| 2004/0102358 A1 | 5/2004 | Scivoletto | ....................... | 514/1 |

FOREIGN PATENT DOCUMENTS

| | | | |
|---|---|---|---|
| EP | 000405067 A2 * | 2/1991 | |
| ZA | 9905262 | * | 4/2000 |

OTHER PUBLICATIONS

Alternate Medicine Network: ViaGirl Women's Pleasure Enhancer, URL <http://web.archive.org/web/20030207090059/www.altmednetwork.net/WomensHealth/viagirl.htm, pp. 1-6.*
Burnett A.L., Chang, A.G., Crone, J.K., Huang, P.L., Sezen, S.F., Noncholinergic Penile Erection in Mice lacking the gene for endothelial nitric oxide synthase. J. Andrology 23(1):92-97 (2002).
Cellek S, Moncada S, Nitrergic neurotransmission mediates the non-adrenergic non-cholinergic responses in the clitoral corpus cavernosum of the rabbit. Br. J. Pharmacol. 125(8):1627-9 (1998).
Christianson DW, Arginase: structure, mechanism, and physiological role in male and female sexual arousal. Acc. Chem. Res. 38(3):191-201 (2005).
Elsner, P., Maibach, H.I. Cutaneous response to topical methyl nicotinate in human forearm and vulvar skin. J. Dermatol. Sci. 2(5):341-5 (1991).
Gonzalez-Cadavid NF, Rajfer J, Therapy of erectile dysfunction. Endocrine 23(2-3):167-76 (2004).
Gragasin FS, Michelakis ED, Hogan A, Moudgil R, Hashimoto K, Wu X, Bonnet S, Haromy A, Archer SL, The neurovascular mechanism of clitoral erection: nitric oxide and cGMP-stimulated activation of BKCa channels. FASEB J. 18(12):1382-91 (2004).
Guy, RH, Maibach, HI., Rapid radial transport of methyl nicotinate in the dermis, Archives Dermatol. Res. 273:91-95 (1982).
Irritants, Rubefacients and Vesicants, in Remington's Pharmaceutical Sciences 17th Edition, Mack Publishing Company, Eaton, Pennsylvania, p. 782, (1985).

(Continued)

*Primary Examiner*—Patricia Leith
(74) *Attorney, Agent, or Firm*—Sheridan Ross, P.C.

(57) ABSTRACT

A topical composition which enhances sexual responsiveness of a mammal is disclosed. An effective dosage of a peripheral vasodilator, an absorption enhancer and, optionally, a vasoconstrictor and an alpha receptor blocker are combined with a pharmaceutically-acceptable topical vehicle to produce the composition. The compositions are applied topically to the penis or labia majora and minora pudenda to enhance erection or vasocongestion.

4 Claims, No Drawings

OTHER PUBLICATIONS

Ito TY, Trant AS, Polan ML., A double-blind placebo-controlled study of ArginMax, a nutritional supplement for enhancement of female sexual function. J. Sex Martial Ther. 27(5):541-9 (2001).

Kim NN, Christianson DW, Traish AM, Role of arginase in the male and female sexual arousal response. J. Nutr. 134(10 Suppl):2873S-2879S; dicussion 2895S (2004).

Klotz, T. Mathers, M.J. Braun, M., Bloch, W., Englemann, U. Effectiveness of oral L-arginine in first-line treatment of erectile dysfunction in a controlled crossover study. Urol. Int. 63(4):220-23 (1999).

Lebret, T, Herve JM, Gorny P, Worcel M, Botto H., Efficacy and safety of a novel combination of L-arginine glutamate and yohlmbine hydrochloride: a new oral therapy for erectile dysfunction. Eur. Urol. 41(6):608-13; discussion 613 (2002).

McKay, D., Nutrients and botanicals for erectile dysfunction: examining the evidence. Altern. Med. Rev. 9(1):4-16 (2004).

Meston CM, Worcel M, The effects of yohimbine plus L-arginine glutamate on sexual arousal in postmenopausal women with sexual arousal disorder. Arch. Sex Behav. 31(4):323-32 (2002).

Moncada S., Higgs EA. Molecular mechanisms and therapeutic strategies related to nitric oxide. FASEB 9:1319-1330 (1995).

Muller, B., Kasper, M., Surber, C., Imanidis G., Permeation, metabolism and site of action concentration of nicotinic acid derivatives in human skin Correlation with topical pharmacological effect. Eu. J. Pharm. Sci. 20:181-95 (2003).

Park JK, Kim SZ, Kim SH, Kim YG, Cho KW, Renin angiotensin system of rabbit clitoral cavernosum: interaction with nitric oxide. J. Urol. 164(2):556-61 (2000).

Park JK, Kim JU, Lee SO, Hwang PH, Yi HK, Kim YG, Cho KW, Nitric oxide-cyclic GMP signaling pathway in the regulation of rabbit clitoral cavernosum tone. Exp. Biol. Med. 227(11):1022-30 (2002).

Sample of CONNECTION™ packaging including ingredient list, enclosed herewith.

Sivamani RK, Stoeber B, Wu GC, Zhai H, Liepmann D, Maibach H., Clinical microneedle injection of methyl nicotinate: stratum corneum penetration. Skin Res. Technol. 11(2):152-6 (2005).

Stanislavov R, Nikolova V., Treatment of erectile dysfunction with pycnogenol and L-arginine. J. Sex Marital Ther. 29(3):207-13 (2003).

Web page from the Better Business Bureau of Metropolitan New York, Inc., Apr. 21, 2005.

Woolfson AD, Malcolm RK, Campbell K, Jones DS, Russell JA., Rheological, mechanical and membrane penetration properties of novel dual drug systems for percutaneous delivery. J Control Release. 3;67(2-3):395-408 (2000).

* cited by examiner

TOPICAL COMPOSITIONS FOR ENHANCING SEXUAL RESPONSIVENESS

CROSS REFERENCE TO RELATED APPLICATION

This application claims priority under 35 U.S.C. § 119(e) to U.S. Provisional Patent Application Ser. No. 60/445,624, filed as Feb. 7, 2003 which is incorporated herein in its entirety by this reference.

FIELD OF THE INVENTION

The invention relates to a topically-administered compositions for the enhancement of sexual responsiveness in mammals.

BACKGROUND OF THE INVENTION

The male sexual response includes the filling of vascular channels that are empty in the flaccid penis, with blood at pressures approaching systemic levels. Erection occurs when the arteriolar and sinusoidal smooth muscles of the vessels within the corpora relax, thus lowering resistance in these channels and allowing arterial blood to surge into the penis. Exit of the arterial blood is simultaneously impeded by an increase in venous resistance. Further distention of the sinusoids is restrained by the minimally distensible tunica albuginea that raises the pressure further and also restricts venous outflow. Thus, the corpora cavernosa and corpus spongiosum can be filled with blood and the penis can be erect with little demand on cardiac output. These vascular changes that occur during erection are thought to be controlled by vasoactive intestinal polypeptide, perhaps aided by alpha-adrenergic blockade, acetylcholine and nitric oxide.

The female sexual response cycle is typically divided into four phases including desire, excitement, which includes physiological changes such as vasocongestion in the pelvis, vaginal lubrication, and expansion and swelling of the external genitalia, orgasm, and resolution. Disorders of female sexual desire or response are estimated to affect from 30 to 50 percent of the adult female population. These disorders may have a variety of causes including psychogenic etiologies, anatomical disorders, drug-induced disorders, diabetes mellitus, post-surgical disorders, atherosclerosis, post-traumatic disorders, as well as endocrine etiologies. Depending upon the etiology of the disorder, effective treatment may be had by overcoming any boundaries to the physiological changes that take place during excitement including vasocongestion. Thus, in certain cases, it may be possible to enhance the female sexual response by stimulating vasocongestion.

There are a wide variety of pharmacological agents used for the enhancement of erection and treatment of sexual dysfunction and as pro-libido agents. Some examples include: serotonin receptor agonists and antagonists (see, e.g., EP 385,658; WO 94/15,920; GB 2,248,449; and GB 2,276,165), dopamine receptor agonists (see, e.g., WO 93/23,035; WO 94/21,608; Pomerantz S. M., Pharmacol. Biochem. Behav. 39:123–128, 1991; and Ferrari F. et al. Psychopharmacology 113:172–176, 1993); adrenergic receptor agonists (see, e.g., WO 95/13,072; EP 611,248; U.S. Pat. No. 5,229,387; and WO 92/11,851); inhibitors of phoshodiesterase (see, e.g., DE 4,338,948; and WO 94/28, 902); histamine receptor agonists (see, e.g., U.S. Pat. Nos. 4,013,659; 4,126,670; 4,767,778; WO 91/17,146; U.S. Pat. No. 5,047,418; and EP 0,458,661); neuropeptide Y antagonists (see, e.g., WO 95/00,161); angiotensin II receptor antagonists (see, e.g., EP 577,025); cholinesterase inhibitors (see, e.g., U.S. Pat. Nos. 5,177,070; and 4,633,318); combinations of agents with the different types of biological activity (see, e.g., U.S. Pat. No. 5,145,852; and WO 95/05, 188); derivatives of vasoactive intestinal peptide (see, e.g., U.S. Pat. No. 5,147,855; EP 540,969; and EP 463,450); prostaglandins (see, e.g., WO 93/00,894; and EP 459,3770); antidepressants and antipsychotics (see, e.g., U.S. Pat. No. 4,931,445; GB 2,448,449; and Naganuma et al. Clin. Exp. Pharm. Physiol. 20:177–183, 1993); nitric oxide donors (see, e.g., WO 92/21,346; DE 4,305,881; DE 4,212,582; and WO 94/16,729); calcitonin gene related peptide (see, e.g., Steif, C.G. et al., Urology, 41:397–400, 1993); and androgens (see, e.g., JP 06,211,675; HU 62,473; and WO 94/16, 709). Unfortunately, many or all of these pharmacological agents are associated with adverse effects including aggravation or induction of schizophrenia, serotonin syndrome, central nervous system and endocrine system dysfunction, pain, echytomosis and priapism.

Accordingly there is a need in the art to identify new pharmacological agents or compositions which are useful for enhancement of the sexual response in mammals.

SUMMARY OF THE INVENTION

One embodiment of the present invention provides a topical composition comprising at least one active ingredient including methyl nicotinate, yohimbe, L-arginine in a pharmaceutically-acceptable topical vehicle. These compositions may also include as least one additional active ingredient including muira puama, catuaba, maca extract, and saw palmetto. In a preferred embodiment, the composition contains methyl nicotinate, yohimbe, L-arginine, muira puama, catuaba, maca extract, saw palmetto, nettles and zinc. In another preferred embodiment, the composition contains methyl nicotinate, L-arginine, muira puama, catuaba, maca extract, nettles and zinc.

In a particularly preferred embodiment, the compositions contains between about 0.1% and about 5% methyl nicotinate, between about 5 drops and about 50 drops of yohimbe extract, between about 0.3% and about 1.5% L-arginine; between about 1 drop and about 30 drops of muira puama extract per four ounces of composition, between about 1 drop and about 30 drops of catuaba extract per four ounces of composition, between about 1 drop and about 30 drops of maca extract per four ounces of composition, and between about 1 drop and about 30 drops of saw palmetto extract per four ounces of composition in a pharmaceutically-acceptable topical vehicle.

Preferably, the compositions of the present invention are formulated in a topical lotion containing aloe and vitamin E.

Another preferred embodiment is a condom having an internal surface coated with one of the topical compositions of the present invention.

In another particularly preferred embodiment of the present invention the topical composition contains about 1% methyl nicotinate, about 25 drops of yohimbe extract, about 8 mg/cm$^3$ of L-arginine, about 12 drops of muira puama extract, about 12 drops of catuaba extract, about 12 drops of maca extract, and about 12 drops of saw palmetto extract in a pharmaceutically-acceptable water-based topical vehicle containing aloe and vitamin E.

In another particularly preferred embodiment of the present invention, the topical composition contains about 1% methyl nicotinate, about 8 mg/ml of L-arginine, about 12 drops of muira puama extract, about 12 drops of catuaba extract, and about 12 drops of maca extract, in a pharmaceutically-acceptable water-based topical vehicle containing aloe and vitamin E.

DETAILED DESCRIPTION OF THE INVENTION

As used herein, the transitional phrases "comprising", "consisting essentially of" and "consisting of" define the scope of the appended claims with respect to what un-recited additional components, if any, are excluded from the scope of the claim. The term "comprising" is intended to be inclusive or open-ended and does not exclude additional, un-recited elements or method steps. The phrase "consisting of" excludes any element, step, or ingredient not specified in the claim. The phrase "consisting essentially of" limits the scope of a claim to the specified materials or steps and those that do not materially affect the basic and novel characteristic(s) of the claimed invention. All compositions or formulations identified herein can, in alternate embodiments, be more specifically defined by any of the transitional phrases "comprising", "consisting essentially of" and "consisting of."

The two most important denominators to the erection process and penis size are blood flow and vessel size. The compositions of the present invention are formulated with a combination of active ingredients that enhance blood flow to the area applied thereby resulting in erection or vasocongestion. The active ingredients in these compositions aid the body in the production of nitric oxide via the essential amino acid L-arginine. Additionally, these compositions function as powerful vasodilators using yohimbe, and methyl nicotinate to increase circulation, discourage clot formation, and reinforce the walls of the capillaries allowing for bigger, thicker blood vessels. These physiological actions are believed to be useful for the treatment of sexual dysfunction resulting from circulatory disorders. Additionally, these physiological actions are believed to strengthen blood vessel walls of the penis resulting in erectile enhancement. Further, herbal ingredients in these compositions can act to promote and enhance desire functioning as pro-libido agents.

The compositions of the present invention contain one or more of the following active ingredients: methyl nicotinate, yohimbe extract, panax ginseng, L-arginine, muira puama, catuaba bark, maca, and saw palmetto.

Methyl nicotinate is rubefacient and counterirritant for the relief of aches and pains in muscles, tendons, and joints. When applied to the skin, methyl nicotinate causes vasodilation of the surrounding blood vessels producing a feeling of warmth. This sensation competes with, and to some extent blocks, pain in underlying muscles and joints, since both feelings are conveyed by the same nerves. The compositions of the present invention may contain between about 0.1% and about 5% methyl nicotinate. Preferably, the compositions of the present invention contain between about 0.5% and about 2% methyl nicotinate. Most preferably, the compositions of the present invention contain about 1% methyl nicotinate. Suitable sources of methyl nicotinate for use in compositions of the present invention are available commercially. For example, methyl nicotinate is available commercially from Araer Chemicals.

Yohimbe is a vasodilator used as a sensual stimulant for healthy men and women and to treat organic impotence. Yohimbe is thought to stimulate the pelvic nerve ganglia and is thus useful for the treatment of erection problems. Effects may include increased libido, increased sensation and increased stamina. The compositions of the present invention may include yohimbe extract prepared by extracting the yohimbe for one ounce of a plant material containing the herb into two ounces of a suitable liquid. Typically the extraction liquid is water or an alcohol. Prepared in this manner, compositions of the present invention may contain between about 5 drops and about 50 drops of the yohimbe extract in 120 $cm^3$ of the topical composition of the present invention. Preferably, the compositions of the present invention contain between about 15 drops and about 35 drops of the yohimbe extract in four ounces of the topical composition. Most preferably, the compositions of the present invention contain about 25 drops of the yohimbe extract in four ounces of the topical composition. Herbal extracts containing yohimbe that are suitable for use in formulating compositions of the present invention are available commercially. For example, an herbal blend containing yohimbe that is suitable for use in compositions of the present invention is commercially available from Nature's Alternative.

Panax ginseng is an herb thought to be an immune stimulant. Ginseng has a high content of the Rg1 group of ginsenosides which cause an increase in motor activity. It acts on the adrenal and pituitary glands and is thought to improve response to stress, increase mental and physical work capacity, increase concentration and mental activity, enhance mental acuity and intellectual and physical performance and benefit the immune system. The compositions of the present invention may include ginseng extract prepared by extracting ginseng from one ounce of a plant material containing the herb into two ounces of a suitable liquid. Typically the extraction liquid is water or an alcohol. Prepared in this manner, compositions of the present invention may contain between about 1 drop and about 30 drops of ginseng extract in four ounces of the topical composition. Preferably, the compositions of the present invention contain between about 5 drops and about 20 drops of ginseng extract in four ounces of the topical composition. Most preferably, the compositions of the present invention contain about 12 drops of ginseng extract in four ounces of the topical composition. Herbal extracts containing ginseng that are suitable for use in formulating compositions of the present invention are available commercially. For example, an herbal blend containing ginseng that is suitable for use in compositions of the present invention is commercially available from Nature's Alternative.

L-arginine is an essential amino acid with vasodilatory properties. L-arginine is the primary nutrient that allows the body to create nitric oxide, which helps regulate every physiologic function in the body. L-arginine has been shown to reduce blood pressure, improve heart function, circulation, lower cholesterol, improve immune system response, wound healing, open airways in asthma and help with male sexual function. When arginine is introduced into the body, it interacts with the enzyme nitric oxide synthase which replaces a nitrogen molecule on arginine with an oxygen atom forming nitric oxide. The compositions of the present invention may contain between about 100 mg and about 400 mg of L-arginine per ounce of the topical composition. Preferably, the compositions of the present invention contain between about 200 mg and about 300 mg of L-arginine per ounce of the topical composition. Most preferably, the compositions of the present invention contain about 240 mg of L-arginine per ounce of the topical composition. L-arginine suitable for use in formulating compositions of the present invention is available commercially. For example, a commercial source of L-arginine that is suitable for use in compositions of the present invention is commercially available from T.J. Clark.

Muira puama is a botanical isolated from a tree that grows in the rain forests of Brazil. Used as a mild tonic, this herb is thought to be useful in treating the symptoms of nervous problems and disorders such as neurasthenia, neuralgia and nervous depression. The compositions of the present invention may include muira puama extract prepared by extracting one ounce of muira puama plant material into two ounces of a suitable liquid. Typically the extraction liquid is an alcohol. Prepared in this manner, compositions of the present invention may contain between about 1 drop and about 30 drops of muira puama extract in four ounces of the topical composition. Preferably, the compositions of the present invention contain between about 5 drops and about 20 drops of muira puama extract in four ounces of the topical composition. Most preferably, the compositions of the present invention contain about 12 drops of muira puama extract in four ounces of the topical composition. Herbal extracts of muira puama that are suitable for use in formulating compositions of the present invention are available commercially. A concentrated extract that is suitable for use in compositions of the present invention is commercially available from Raintree Nutrition.

Catuaba is a botanical extracted from the plant species *Juniperis brasilinsis* native to Brazil. It is reported to have benefits in relieving insomnia from hypertension, restless sleeping patterns and in helping to arrest failing memory. The compositions of the present invention may include catuaba extract prepared by extracting one ounce of catuaba bark into two ounces of a suitable liquid. Typically the extraction liquid is water or an alcohol. Prepared in this manner, compositions of the present invention may contain between about 1 drop and about 30 drops of catuaba extract in four ounces of the topical composition. Preferably, the compositions of the present invention contain between about 5 drops and about 20 drops of catuaba extract in four ounces of the topical composition. Most preferably, the compositions of the present invention contain about 12 drops of catuaba extract in four ounces of the topical composition. Herbal extracts containing catuaba that are suitable for use in formulating compositions of the present invention are available commercially. For example, a catuaba bark extract suitable for use in compositions of the present invention is commercially available from Raintree Nutrition.

Maca is a plant also known as *Lepidium meyenii*. Peruvian maca root is a vegetable root or tuber related to the potato and the Mexican wild yam. It contains amino acids, complex carbohydrates, vitamins B 1, B2, B 12, C and E and minerals, including calcium, phosphorus, zinc, magnesium and iron. This herb has traditionally been used to increase energy, vitality, stamina and endurance in athletes, promote mental clarity, as an aphrodisiac for both men and women, for male impotence, menstrual irregularities and female hormone imbalances, including menopause. The compositions of the present invention may include maca extract prepared by extracting one ounce of maca plant root material into two ounces of a suitable liquid. Typically the extraction liquid is water or an alcohol. Prepared in this manner, compositions of the present invention may contain between about 1 drop and about 30 drops of maca extract in four ounces of the topical composition. Preferably, the compositions of the present invention contain between about 5 drops and about 20 drops of maca extract in four ounces of the topical composition. Most preferably, the compositions of the present invention contain about 12 drops of maca extract in four ounces of the topical composition. Maca plant material suitable for use in preparing extracts for use in formulating compositions of the present invention are available commercially. For example, bulk maca plant material that is suitable for use in compositions of the present invention is commercially available from Raintree Nutrition.

Saw Palmetto is an urinary antiseptic also known as *Serenoa repens*. This herb acts to tone and strengthen the male reproductive system and is used in cases of enlarged prostate gland. The compositions of the present invention may include saw palmetto extract prepared by extracting the saw palmetto from one ounce of a plant material containing the herb into two ounces of a suitable liquid. Typically the extraction liquid is water or an alcohol. Prepared in this manner, compositions of the present invention may contain between about 1 drop and about 30 drops of saw palmetto extract in four ounces of the topical composition. Preferably, the compositions of the present invention contain between about 5 drops and about 20 drops of saw palmetto extract in four ounces of the topical composition. Most preferably, the compositions of the present invention contain about 12 drops of saw palmetto extract in four ounces of the topical composition. Herbal extracts containing saw palmetto that are suitable for use in formulating compositions of the present invention are available commercially. For example, a saw palmetto extract that is suitable for use in compositions of the present invention is commercially available from Nature's Alternative.

The compositions of the present invention can optionally include as active ingredients nettles and/or zinc. The components are widely available commercially.

The compositions of the present invention may contain other ingredients that are not physiologically active but serve to enhance the pharmaceutical elegance of the final topical composition. For example, the compositions of the present invention may contain excipients such as lactose, dextrose, sucrose, sorbitol, mannitol, starch, gum acacia, calcium silicate, microcrystalline cellulose, polyvinylpyrrolidinone, cellulose, water, syrup, and methyl cellulose. Additionally, the compositions of the present invention may include lubricating agents such as talc, magnesium stearate and mineral oil, wetting agents, emulsifying and suspending agents, preserving agents such as methyl- and propylhydroxybenzoates, sweetening agents or flavoring agents.

The compositions of the present invention may be formulated in any pharmaceutically acceptable topical vehicle that does not interact adversely with the active ingredients or, in the case of the embodiment which includes a coating of the compositions applied to one surface of a condom, does not interact adversely with the condom materials. For example, compositions of the present invention may be formulated in water or oil based topical vehicles. These compositions can include lanolin, aquaphor, methylcellulose and derivatives thereof, petroleum based vehicles, aloe and the like. Preferably, the compositions of the present invention are formulated in a topical, water-based vehicle containing aloe and vitamin E. Suitable topical vehicles containing aloe and vitamin E are available commercially. For example, a suitable topical vehicle for use in formulating compositions of the present invention containing aloe and vitamin E is available from T.C. Laboratories (Treasures Company).

Preferably, the topical compositions of the present invention contain a mixture of distilled water, aloe barbadensis leafjuice, helianthus annus (sunflower) seed oil, stearic acid, glycine soja (soybean) oil, cetyl alcohol NF, emulsifying wax, olea Europaea (olive) fruit oil, glycerin, palmitic acid, cymbopogan schoenanthus (lemongrass) oil, mentha piperita (peppermint) oil, tocopherol, denatured alcohol, methyl salicylate, aloe barbadensis leaf extract, menthol, fragrance, camella sinensis (green tea) leaf extract, rosmarinus officinalis (rosemary) leaf extract, citrus grandis (grapefruit) seed extract, lecithin, sodium bicarbonate, ascorbyl palmitate, polysorbate 20, methylparaben, propylparaben, urtica dioica (nettles) extract or zinc oxide, having a pH of between about 5.0 and about 8.

The compositions of the present invention are formulated for transdermal delivery of the active ingredients following topical administration to the penis or labia majora and minora pudendi. A small amount of the compositions of the present invention is applied topically directly to the penis or labia majora and minora pudendi. Alternatively, in a preferred embodiment, the composition may be packaged as a coating on the interior surface of a condom. Thereby, upon use of the condom, the composition is applied topically to the penis.

EXAMPLES

Example 1

A preferred embodiment of the topical compositions of the present invention consists essentially of the following ingredients of a quality and purity suitable for topical application to a mammal:

| Active ingredient | Amount per 30 g ± 10% |
| --- | --- |
| methyl nicotinate | 0.3 g |
| yohimbe extract | 25 drops |
| L-arginine | 240 mg |
| muira puama extract | 12 drops |
| catuaba bark extract | 12 drops |
| maca extract | 12 drops |
| saw palmetto | 12 drops |

These active ingredients were formulated in a base for topical administration in a pharmaceutically-acceptable topical vehicle containing distilled water, aloe barbadensis leafjuice, helianthus annus (sunflower) seed oil, stearic acid, glycine soja (soybean) oil, cetyl alcohol NF, emulsifying wax, olea Europaea (olive) fruit oil, glycerin, palmitic acid, cymbopogan schoenanthus (lemongrass) oil, mentha piperita (peppermint) oil, tocopherol, denatured alcohol, methyl salicylate, aloe barbadensis leaf extract, camella sinensis (green tea) leaf extract, rosmarinus officinalis (rosemary) leaf extract, citrus grandis (grapefruit) seed extract, lecithin, sodium bicarbonate, ascorbyl palmitate, polysorbate 20, methylparaben, propylparaben, urtica dioica (nettles) extract and zinc oxide, having a pH of about 6.0.

Example 2

A preferred embodiment of the topical compositions of the present invention consists essentially of the following ingredients of a quality and purity suitable for topical application to a mammal:

| Active ingredient | Amount per 30 g ± 10% |
| --- | --- |
| methyl nicotinate | 0.3 g |
| L-arginine | 240 mg |
| muira puama extract | 12 drops |
| catuaba bark extract | 12 drops |
| maca extract | 12 drops |

These active ingredients were formulated in a base for topical administration in a pharmaceutically-acceptable topical vehicle containing distilled water, aloe barbadensis leafjuice, helianthus annus (sunflower) seed oil, stearic acid, glycine soja (soybean) oil, cetyl alcohol, emulsifying wax, olea europaea (olive) fruit oil, glycerin, palmitic acid, fragrance, tocopherol, denatured alcohol, methyl salicylate, aloe barbadensis leaf extract, camella sinensis (green tea) leaf extract, rosmarinus officinalis (rosemary) leaf extract, citrus grandis (grapefruit) seed extract, lecithin, sodium bicarbonate, ascorbyl palmitate, polysorbate 20, menthol, methylparaben, propylparaben, urtica dioica (nettles) extract and zinc oxide, having a pH of about 6.0.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A composition for topical administration to a mammal comprising, per ounce,
   a. about 1% methyl nicotinate,
   b. about 25 drops of an alcohol extract of yohimbe,
   c. about 8 mg/cm$^3$ of L-arginine,
   d. about 12 drops of an alcohol extract of muira puama,
   e. about 12 drops of an alcohol extract of catuaba,
   f. about 12 drops of an alcohol extract of maca, and
   g. about 12 drops of an alcohol extract of saw palmetto,
   wherein a–g are in a pharmaceutically-acceptable water-based topical vehicle comprising aloe and vitamin E.

2. A composition for topical administration to a mammal comprising,
   a. between about 0.1% and about 5% methyl nicotinate,
   b. between about 0.3% and about 1.5% L-arginine;
   c. between about 1 drop and about 30 drops of an alcohol extract of muira puama,
   d. between about 1 drop and about 30 drops of an alcohol extract of catuaba, and
   e. between about 1 drop and about 30 drops of an alcohol extract of maca,
   wherein a–e are in a pharmaceutically-acceptable topical vehicle.

3. A composition for topical administration to a mammal comprising, per ounce,
  a. about 1% methyl nicotinate,
  b. about 8 mg/cm$^3$ of L-arginine,
  c. about 12 drops of an alcohol extract of muira puama,
  d. about 12 drops of an alcohol extract of catuaba, and
  e. about 12 drops of an alcohol extract of maca,
  wherein a–g are in a pharmaceutically-acceptable water-based topical vehicle comprising aloe and vitamin E.

4. The composition of claim 2, wherein the pharmaceutically-acceptable topical vehicle is a lotion comprising aloe and vitamin E.

* * * * *